United States Patent [19]

Gupta et al.

[11] Patent Number: 5,012,028

[45] Date of Patent: Apr. 30, 1991

[54] PROCESS FOR UPGRADING LIGHT HYDROCARBONS USING OXIDATIVE COUPLING AND PYROLYSIS

[75] Inventors: Victor Gupta; Christopher L. Bodolus, both of Cleveland Heights; Christos Paparizos, Willowick; Wilfrid G. Shaw, Lyndhurst, all of Ohio

[73] Assignee: The Standard Oil Company, Cleveland, Ohio

[21] Appl. No.: 884,474

[22] Filed: Jul. 11, 1986

[51] Int. Cl.$^5$ .............................................. C07C 2/00

[52] U.S. Cl. ................................... 585/500; 585/910

[58] Field of Search ............ 585/500, 943, 310, 910, 585/643

[56] References Cited

U.S. PATENT DOCUMENTS

| | | | |
|---|---|---|---|
| 1,656,813 | 1/1928 | Bird. | |
| 1,863,212 | 6/1932 | Winkler. | |
| 1,922,918 | 8/1933 | Winkler et al. | 260/168 |
| 1,945,960 | 2/1934 | Winkler et al. | 260/170 |
| 1,986,238 | 1/1935 | Winkler et al. | 260/168 |
| 1,988,873 | 1/1935 | Linch et al. | 260/168 |
| 2,436,595 | 2/1948 | Nicholson et al. | 260/666 |
| 2,679,544 | 5/1954 | Bills | 260/679 |
| 2,859,258 | 11/1958 | Fischer et al. | 260/683 |
| 2,885,455 | 5/1959 | Hennig | 585/648 |
| 3,234,300 | 2/1966 | Howard | 260/679 |
| 3,244,765 | 4/1966 | Fauser | 260/679 |
| 3,248,447 | 4/1966 | Lorenz et al. | 260/679 |
| 3,452,114 | 6/1969 | Friz et al. | 260/679 |
| 4,100,218 | 7/1978 | Chin et al. | 260/673 |
| 4,120,910 | 10/1978 | Chu | 260/673 |
| 4,205,194 | 5/1980 | Mitchell et al. | 585/407 |
| 4,433,192 | 2/1984 | Olah | 585/709 |
| 4,443,645 | 4/1984 | Jones et al. | 585/500 |
| 4,489,215 | 12/1984 | Withers | 585/500 |
| 4,495,374 | 1/1985 | Jones et al. | 585/500 |
| 4,507,517 | 3/1985 | Devries et al. | 585/415 |
| 4,513,164 | 4/1985 | Olah | 585/700 |
| 4,520,217 | 5/1985 | Minet | 585/415 |
| 4,523,049 | 6/1985 | Jones et al. | 585/943 |
| 4,533,780 | 8/1985 | Maffia | 585/500 |
| 4,547,607 | 10/1985 | Jones et al. | 585/700 |
| 4,556,749 | 12/1985 | Hazluin | 585/330 |
| 4,560,821 | 12/1985 | Jones et al. | 585/500 |
| 4,567,307 | 1/1986 | Jones et al. | 585/500 |
| 4,608,449 | 8/1986 | Baerns et al. | 585/500 |
| 4,620,057 | 10/1986 | Kimble | 585/500 |
| 4,654,460 | 3/1987 | Kimble | 585/500 |
| 4,658,076 | 4/1987 | Kolts | 585/500 |
| 4,658,077 | 4/1987 | Kolts | 585/500 |

FOREIGN PATENT DOCUMENTS

| | | |
|---|---|---|
| 0189079 | 7/1986 | European Pat. Off. . |
| 85/00141 | 10/1985 | PCT Int'l Appl. . |
| 2148933 | 6/1986 | United Kingdom . |
| 2148935 | 6/1986 | United Kingdom . |

OTHER PUBLICATIONS

PCT International Application No. PCT/US86/01254.
J. Stocki and J. Glowinski, Pr. Nauk, Inst. Technol. Nieorg, Nawozow Miner. Politech. Wroclaw, 24, 43, (1982); Chem. Abstr., 98, 162780e.
Z. Nagy and L. Szepesy, Conf. Chem. Process. Petrol. Natural Gas, Plenary Lect., Budapest, 1965, (Publ. 1968), p. 380; Chem. Abstr., 70, 3166q.
M. Reichert, Erdgas Rohst. Chem. Ind. Erzeng. Redaktionsgasen Huettenw., Symp., 1972, (Publ. 1973), pp. 6, 19; Chem. Abstr., 81, 65955g.
Chiu-Hsun Lin et al., "Oxidative Dimerization of Methane Over Lanthanum Oxide", J. Phys. Chem., 90, 534-537, (1986).
H. M. Smith et al., "Production of Motor Fuels from Natural Gas—I. Preliminary Report on the Pyrolysis of Methane", Report of Investigations, Department of Commerce-Bureau of Mines, R.I. 3143, (Oct., 1931).

Primary Examiner—William R. Dixon, Jr.
Assistant Examiner—James M. Hunter, Jr.
Attorney, Agent, or Firm—Larry W. Evans; Raymond F. Keller

[57] ABSTRACT

A process for converting a gaseous reactant comprising methane or natural gas to higher molecular weight hydrocarbon products is disclosed which comprises: (1) contacting said gaseous reactant with an oxidative coupling catalyst at a reaction temperature in the range of about 500° C. to about 1100° C. for an effective period of time to form an intermediate product comprising ethane, ethylene or a mixture thereof; and (2) pyrolyzing said intermediate product at a temperature in the range of about 900° C. to about 1500° C. for an effective period of time to form said higher molecular weight hydrocarbon products.

22 Claims, 2 Drawing Sheets 5,012,028

PROCESS FOR UPGRADING LIGHT HYDROCARBONS USING OXIDATIVE COUPLING AND PYROLYSIS

TECHNICAL FIELD

This invention relates to a process for upgrading light hydrocarbons. More specifically, this invention relates to a process involving the use of a combination of oxidative coupling and pyrolysis for converting methane or natural gas to higher molecular weight hydrocarbon products.

BACKGROUND OF THE INVENTION

A major source of methane is natural gas. Natural gas at the wellhead typically contains about 40-95% methane depending on the particular source. Other constituents include about 10% ethane with the balance being made up of $CO_2$ and smaller amounts of propane, the butanes, the pentanes, nitrogen, etc.

Primary sources for natural gas are the porous reservoirs generally associated with crude oil reserves. From these sources come most of the natural gas used for heating purposes. Quantities of natural gas are also known to be present in coal deposits and are by-products of crude oil refinery processes and bacterial decomposition of organic matter. Natural gas obtained from these sources is generally utilized as a fuel at the site.

Prior to commercial use, wellhead natural gas must be processed to remove water vapor, condensible hydrocarbons and inert or poisonous constituents. Condensible hydrocarbons are generally removed by cooling natural gas to a low temperature and then washing the natural gas with a cold hydrocarbon liquid to absorb the condensible hydrocarbons. The condensible hydrocarbons are typically ethane and heavier hydrocarbons. This gas processing can occur at the wellhead or at a central processing station. Processed natural gas typically comprises a major amount of methane, and minor amounts of ethane, propane, the butanes, the pentanes, carbon dioxide and nitrogen. Generally, processed natural gas comprises from about 70% to more than about 95% by volume of methane. Natural gas is used principally as a source of heat in residential, commercial and industrial service.

Most processed natural gas is distributed through extensive pipeline distribution networks. As natural gas reserves in close proximity to gas usage decrease, new sources that are more distant require additional transportation. Many of these distant sources are not, however, amenable to transport by pipeline. For example, sources that are located in areas requiring economically unfeasible pipeline networks or in areas requiring transport across large bodies of water are not amenable to transport by pipeline. This problem has been addressed in several ways. One such solution has been to build a production facility at the site of the natural gas deposit to manufacture one specific product. This approach is limited as the natural gas can be used only for one product, preempting other feasible uses. Another approach has been to liquefy the natural gas using cryogenic techniques and transport the liquid natural gas in specially designed tanker ships. Natural gas can be reduced to 1/600th of the volume occupied in the gaseous state by such cryogenic processing, and with proper procedures, safely stored or transported. These processes, which involve liquefying natural gas at a temperature of about $-162°$ C., transporting the gas, and revaporizing it are complex and energy intensive.

Pyrolysis processes involving the conversion of methane to higher molecular weight hydrocarbons at high temperatures, in excess of about 1200° C., are known. These processes are, however, energy intensive and have not been developed to the point where high yields are obtained even with the use of catalysts. Some catalysts that are useful in these processes (e.g., chlorine) are corrosive under such operating conditions.

U.S. Pat. No. 4,507,517 and U.K. Patent Application GB 2 148 935A disclose catalytic processes for converting methane to $C_2+$ hydrocarbons, particularly hydrocarbons rich in ethylene and/or benzene, at temperatures in excess of 1000° C. and high gas hourly space velocities greater than 3200 $hr^{-1}$. The process disclosed in the '517 patent uses a boron compound containing catalyst. The process disclosed in the U.K. application uses a catalyst containing a metal compound of the Group IA, IIA, IIIA, IVB or Actinide series metals.

Low temperature pyrolysis (e.g., to 250° C. and 500° C.) of hydrocarbon feedstocks to higher molecular weight hydrocarbons is described in U.S. Pat. Nos. 4,433,192; 4,497,970; and 4,513,164. The processes described in these patents utilize heterogeneous systems and solid acid catalysts. In addition to the solid acid catalysts, the reaction mixtures described in the '970 and '164 patents include oxidizing agents. Among the oxidizing agents disclosed are air, $O_2$-$O_3$ mixtures, S, Se, $SO_3$, $N_2O$, NO, $NO_3$, F, etc.

The catalytic oxidative coupling of methane at atmospheric pressure and temperatures of from about 500° C. to 1000° C. has been investigated by G. E. Keller and M. M. Bhasin. These researchers reported the synthesis of ethylene via oxidative coupling of methane over a wide variety of metal oxides supported on an alpha alumina structure in *Journal of Catalysis*, 73, 9-19 (1982). This article discloses the use of single component oxide catalysts that exhibited methane conversion to higher order hydrocarbons at rates no greater than 4%. The process by which Keller and Bhasin oxidized methane was cyclic, varying the feed composition between methane, nitrogen and air (oxygen) to obtain higher selectivities.

Methods for converting methane to higher molecular weight hydrocarbons at temperatures in the range of about 500° C. to about 1000° C. are also disclosed in U.S. Pat. Nos. 4,443,644; 4,443,645; 4,443,646; 4,443,647; 4,443,648; 4,443,649; and 4,523,049.

U.S. Pat. Nos. 4,172,810; 4,205,194; and 4,239,658 disclose the production of hydrocarbons including ethylene, ethane, propane, benzene and the like, in the presence of a catalyst-reagent composition which comprises: (1) a group VIII noble metal having an atomic number of 45 or greater, nickel, or a group Ib noble metal having an atomic number of 47 or greater; (2) a group VIb metal oxide which is capable of being reduced to a lower oxide; and (3) a group IIa metal selected from the group consisting of magnesium and strontium composited with a passivated, spinel-coated refractory support or calcium composited with a passivated, non-zinc containing spinel-coated refractory support. The feed streams used in the processes disclosed in these patents do not contain oxygen. Oxygen is avoided for the purposes of avoiding the formation of coke in the catalyst. Oxygen is generated for the reaction from the catalyst; thus periodic regenerations of the catalysts are required.

U.S. Pat. No. 4,450,310 discloses a methane conversion process for the production of olefins and hydrogen comprising contacting methane in the absence of oxygen and in the absence of water at a reaction temperature of at least 500° C. with a catalyst comprising the mixed oxides of a first metal selected from lithium, sodium, potassium, rubidium, cesium and mixtures thereof, a second metal selected from beryllium, magnesium, calcium, strontium, barium, and mixtures thereof, and optionally a promoter metal selected from copper, rhenium, tungsten, zirconium, rhodium, and mixtures thereof.

U.S. Pat. No. 4,560,821 discloses a continuous method for synthesizing hydrocarbons from a methane source which comprises contacting methane with particles comprising an oxidative synthesizing agent under synthesis conditions wherein particles recirculate between two physically separate zones: a methane contact zone and an oxygen contact zone. These particles are maintained in each of the two zones as fluidized beds of solids. The oxidative synthesizing agents are reducible oxides of metals selected from the group consisting of Mn, Sn, In, Ge, Pb, Sb and Bi.

PCT International Application No. PCT/GB85/00141 discloses a process for the production of synthesis gas and higher molecular weight hydrocarbons in which a saturated hydrocarbon and an oxygen containing gas having a ratio of hydrocarbon to oxygen of greater than the stoichiometric ratio for complete combustion are introduced into a bed of an inert particulate material, the upward flow rate of the hydrocarbon/oxygen containing gas stream being sufficient to fluidize or to produce a spouting action of the bed material, whereby at least a part of the particulate material is thrown up above the bed surface and subsequently falls back into the bed, the hydrocarbon and oxygen containing gas being ignited and reacted together, and the products of the reaction being withdrawn.

SUMMARY OF THE INVENTION

The present invention provides for a process for converting a gaseous reactant comprising methane or natural gas to higher molecular weight hydrocarbon products comprising: (1) contacting said gaseous reactant with an oxidative coupling catalyst at a reaction temperature in the range of about 500° C. to about 1100° C. for an effective period of time to form an intermediate product comprising ethane, ethylene or a mixture thereof; and (2) pyrolyzing said intermediate product at a temperature in the range of about 900° C. to about 1500° C. for an effective period of time to form said higher molecular weight hydrocarbon products.

DESCRIPTION OF THE PREFERRED EMBODIMENT

The Oxidative Coupling Catalyst

Figure 1:
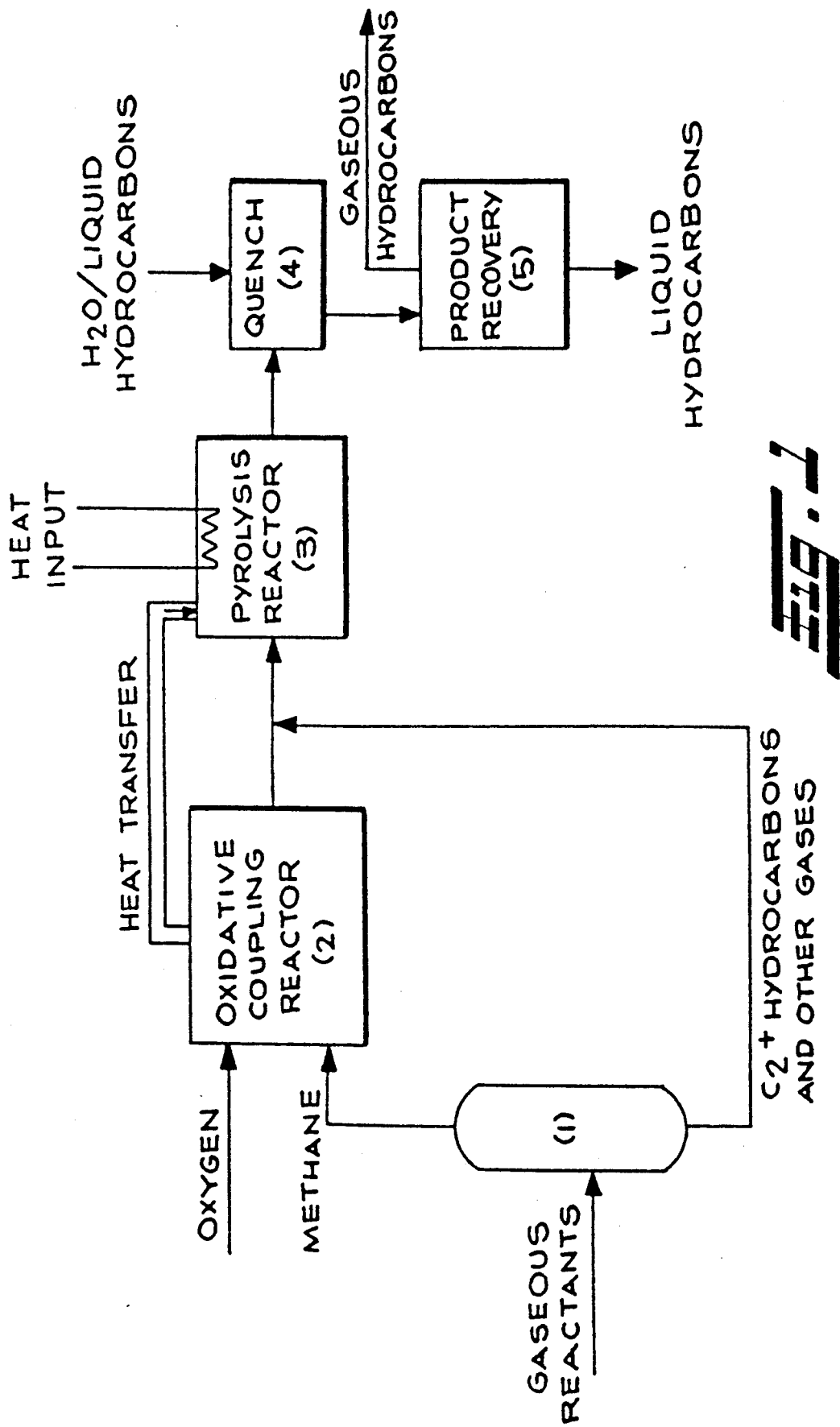
FIG. 1 is a flow sheet illustrating the operation of the process of the invention in a preferred manner.

The conversion of the gaseous reactant to higher molecular weight hydrocarbons in accordance with the invention is accomplished using an oxidative coupling catalyst. Any oxidative coupling catalyst known in the art can be used. Preferably, the catalyst is a metal oxide other than a reducible metal oxide.

In a particularly advantageous embodiment of the invention the catalyst is selected from those metal oxide complexes represented by the formula $$A_a D_b E_c O_x$$

wherein

A is an alkali metal, Ag, Tl or a mixture of two or more thereof,

D is Mn, Sn, Pb, Sb, Bi, Zn, a rare earth metal (including Sc, Y and La), an alkaline earth metal, or a mixture of two or more thereof, E is Ti, Zr, Hf, Nb, Ta, W, Al, Si, P, Ga, B, or a mixture of two or more thereof, a is a number in the range of zero to about 100, b is a number in the range of about 0.1 to about 100, c is a number in the range of zero to about 100, and x is the number of oxygens needed to fulfill the valence requirements of the other elements.

In a particularly advantageous embodiment of the invention the catalyst is a metal oxide complex represented by the formula $$PbMg_nO_x$$

wherein n is a number in the range of about 0.1 to about 100, preferably about 1 to about 30, more preferably about 10 to about 24, and x is the number of oxygens needed to fulfill the valence requirements of the other elements.

The foregoing oxidative coupling catalysts can be formed in any conventional manner, such as tableting, pelleting, or supporting the metal oxide complex material on a carrier. The catalyst can be in the form of microspheroidal particles or monoliths. Suitable carrier materials include silica, alumina, fused alumina, zirconia, hafnia, titania, magnesia, germanium oxide, silicon carbide, clay, etc. In general, the carrier may be employed in amounts of up to about 99.5% by weight of the final catalyst composition.

The catalysts of the invention may be prepared by coprecipitation or by other methods known in the art. Generally they are prepared by mixing an aqueous solution of compounds containing the metal components, forming a precipitate and drying this precipitate. Examples of the compounds containing the metal components that are useful include but are not limited to oxides, hydroxides, inorganic salts (e.g., nitrates, phosphates, halides, carbonates, silicates, aluminates) and salts of organic acids (e.g., acetates, formates, butyrates, propionates, benzoates and the like). The catalyst may be calcined to produce desirable physical properties such as attrition resistance, optimum surface area and particle size.

The catalyst may be incorporated with the carrier by coating, impregnation or coprecipitation using known techniques. The catalyst can be coprecipitated with one carrier material (e.g., silica) and then the combination of catalyst and carrier can be coated on another carrier material (e.g., Alundum, a product of Norton Co. identified as fused alumina).

A particularly useful coating procedure is disclosed in U.S. Pat. No. 4,077,912, which is incorporated herein by reference. Briefly, this method involves partially wetting the carrier, contacting the partially wetted carrier with a powdered precipitate of the catalytic components, then gently agitating the mixture until the catalytic complex is formed. Agitation is conveniently conducted by placing the partially wetted carrier in a rotating drum and adding the powdered precipitate until none is taken up by the carrier. The liquid used to wet the carrier may include inorganic or organic liquids and is dependent upon the type of catalytic components employed. The liquid and the catalytic components should have a relatively high degree of attraction for each other.

The catalytic components can also be impregnated on the carrier by depositing a solution containing the catalytic components on the carrier using known techniques, then drying and calcining.

The catalytic components may optionally be individually coated or impregnated on a carrier using the above-indicated technique.

In order to further illustrate the preparation of the catalysts of the invention, the following example is provided. In the following example as well as throughout the specification and in the appended claims, all parts and percentages are by weight and all temperatures are in degrees centigrade, unless otherwise indicated.

EXAMPLE 1

$PbMg_{12}O_x$

A slurry was prepared by mixing a solution of 14 grams of lead nitrate in 36 grams of water and 10 grams of concentrated nitric acid (70% $HNO_3$), with 51 grams of magnesium hydroxy carbonate (Baker analyzed 41.2% MgO) in 150 grams of water. The mixture was stirred overnight. A white slurry formed. The pH was 8-8.5. The slurry was stirred and heated until a thick paste was formed. The paste was dried at 110° C. overnight. The resulting dried material was ground and screened. 12 grams (19 cc) of the 20-35 mesh portion of the ground material were heat treated in flowing nitrogen at 375° C. for 2 hours to provide the desired catalyst.

The Upgrading Process

The gaseous reactants that are converted to higher molecular weight hydrocarbons in accordance with the process of the invention comprise methane or natural gas and may include additional hydrocarbons typically containing from 1 to about 5 carbon atoms. These hydrocarbons include, for example, ethane, ethylene, acetylene, propane, propylene, the butanes, the butylenes, the pentanes, the pentylenes, and the like, as well as mixtures of two or more of said hydrocarbons. The gaseous reactants may also include hydrogen sulfide and/or carbon monoxide, as well as hydrocarbons recycled from other parts of the process as discussed more fully below.

In a particularly advantageous embodiment of the invention, the gaseous reactant is natural gas. The natural gas that can be used can be either wellhead natural gas, as discussed above, or processed natural gas. The composition of processed natural gas varies with the needs of the ultimate user. A typical processed natural gas composition contains about 70% by weight methane, about 10% by weight ethane, about 10 to about 15% $CO_2$ and the balance being made up of smaller amounts of propane, butane and nitrogen.

The inventive process involves a combination of oxidative coupling, which is an exothermic reaction, and pyrolysis, which is an endothermic reaction. Sensible heat and coupling products that are generated during the exothermic oxidative coupling reaction can be used in the pyrolysis reaction. An advantage of the invention is that the amount of external heat that is required to effect the pyrolysis phase of the process can be significantly less than with conventional pyrolysis processes. Additionally, the liquid yields that can be realized in the higher molecular weight hydrocarbon products of the invention can be significantly higher than those obtained with conventional oxidative coupling and pyrolysis processes even when compared to the additive yields of these conventional processes when such processes are run independently of one another. This latter advantage is illustrated in the examples discussed below.

The oxidative coupling step can be conducted in the presence or absence of oxygen in the feedstream. If oxygen is not provided in the feedstream, it must be generated by the catalyst. Preferably, however, oxygen is fed to the reactor with the gaseous reactant in the feedstream. Gaseous oxygen may be provided as substantially pure oxygen or diluted with nitrogen, carbon dioxide, carbon monoxide, or other inert gases (e.g., noble gases such as helium, neon, argon, etc.), or may be provided in the form of air. Preferably the feedstream contains from about 50% to about 90% by volume methane. The mole ratio of oxygen to methane preferably ranges from about 0.1 to about 1 mole of oxygen per mole of methane, more preferably from about 0.1 to about 0.5 mole of oxygen per mole of methane. The feedstream can contain from zero up to about 25 moles of nitrogen and/or other inert gases (e.g., noble gases such as helium, neon, argon, etc.), per mole of methane. The feedstream can also contain from zero up to about 25 moles of water per mole of methane.

The catalyst can be regenerated by passing oxygen over it at an elevated temperature. Preferably a mixture of oxygen and an inert gas (e.g., air) is passed over the catalyst at the reaction temperature for a sufficient period of time (e.g., 15 minutes) to reoxidize the catalyst. When oxygen or an oxygen source is provided in the feedstream, regeneration is not required or at least not required as often as with processes that do not employ oxygen in the feedstream.

The inventive process can be carried out by contacting the gaseous reactant with one of the catalysts described above in a fluid bed reactor, fixed bed reactor, spouted bed or any other suitable reactor configuration such as a moving bed reactor, swing reactor system or membrane reactor. The reaction can be conducted in a continuous or a batch-type mode. The reaction temperature for the oxidative-coupling step is preferably in the range of about 500° C. to about 1100° C., more preferably from about 700° C. to about 950° C. The average contact time of the gaseous reactants with the oxidative-coupling catalyst is preferably from about 1 millisecond to about 1500 milliseconds, more preferably from about 20 milliseconds to about 1000 milliseconds, more preferably about 75 milliseconds to about 300 milliseconds.

The product of the oxidative coupling step is an intermediate product which comprises ethylene, ethane or a mixture thereof. This intermediate product may also comprise other higher molecular weight hydrocarbons (e.g., $C_3+$ hydrocarbons) as well as by-product water, carbon monoxide and carbon dioxide. Unconverted methane can be recycled through the catalyst so as to increase the overall yield of $C_2+$ hydrocarbons in the intermediate product.

Pyrolysis is effected by heating the intermediate product in a reactor at a temperature that is preferably in the range of about 900° C. to about 1500° C., more preferably about 950° C. to about 1300° C., more preferably about 1000° C. to about 1200° C. The pyrolysis reactor can be of any conventional design that is adapted to the specific reactants and high molecular weight products provided for in the process of the invention. These reactors include fired tubular reactors, pebble bed heaters and regenerative furnaces, with the fired tubular reactors being particularly preferred. These reactors can be made from a variety of materials having temperature stability and thermal conductivity characteristics required by the process of the invention, these materials including, for example, silicon carbide, quartz, alumina, etc. The design and construction of such apparatus is discussed more fully below. The residence time of the gases in the pyrolysis reactor is preferably in the range of about 1 to about 1500 milliseconds, more preferably about 20 to about 1000 milliseconds.

Preferably, the intermediate product and the catalyst are separated prior to pyrolysis. This separation can involve providing a separate oxidative-coupling zone and a separate pyrolysis zone within the same reactor, or it can involve providing separate reactors, one for the oxidative-coupling step and one for the pyrolysis step.

The pressure for both the oxidative-coupling step and the pyrolysis step can range from atmospheric pressure up to about 40 atmospheres, preferably from atmospheric pressure up to about 4 atmospheres.

The process of the invention can be more readily understood by referring to FIG. 1. In FIG. 1, the gaseous reactants are advanced to a separation column (1) wherein methane is separated from the higher hydrocarbons and other gases. The methane is then advanced to the oxidative-coupling reactor (2). Oxygen or an oxygen source is mixed with the methane. Preferably, the methane and oxygen are premixed prior to advancement to the oxidative-coupling reactor. The methane and oxygen are also preferably preheated to a temperature of up to about 700° C., more preferably in the range of about 200° C. to about 700° C. In the oxidative-coupling reactor (2), the methane and oxygen contact the oxidative-coupling catalyst at a temperature in the range of about 500° C. to about 1100° C., preferably about 700° C. to about 950° C., for an effective period of time to form an intermediate product comprising ethane, ethylene or a mixture thereof. The intermediate product may also contain acetylene as well as higher molecular weight products such as hydrocarbons having from about 3 to about 5 carbon atoms per molecule. The effluent from the oxidative-coupling reactor (2) consists of the intermediate product and unreacted gaseous reactants. Sensible reaction heat from the oxidative coupling reaction is also present in this effluent. The higher hydrocarbons and other gases from the separation column (1) are preferably mixed with the effluent from the oxidative-coupling reactor (2) and the resulting mixture is then advanced to the pyrolysis reactor (3). Alternatively, the step of mixing the higher hydrocarbons and other gases from the separation column (1) with the effluent from the oxidative-coupling reactor (2) can be avoided. The pyrolysis reactor (3) can be separated from or integrally formed with the oxidative-coupling reactor (2). Exothermic heat from the oxidative-coupling reactor (2) increases the temperature of the effluent from such oxidative coupling reactor to a temperature in the range of about 800° C. to about 1400° C., preferably about 900° C. to about 1200° C. This temperature increase substantially reduces and in some instances can eliminate the external heat required for the pyrolysis reactor. External heat can be applied to the pyrolysis reactor to supplement the heat provided from the oxidative-coupling reaction. The higher molecular weight hydrocarbons in the intermediate product that emerges as a gaseous effluent from the oxidative coupling reactor also significantly increase the yield of desirable liquid products from the pyrolysis reactor (3). The effluent stream from the pyrolysis reactor (3) is advanced to quench tower (4) wherein the effluent stream is rapidly cooled to ambient temperatures to avoid degradation of the higher molecular weight hydrocarbon products to undesirable carbon products. In the quench tower (4), cooling is effected by direct mixing of the effluent stream with water or liquid hydrocarbons. The higher molecular weight hydrocarbon products and the quenching liquid are then advanced to the product recovery unit (5) wherein liquid hydrocarbons, which are preferably hydrocarbon products of five or more carbon atoms per molecule, are separated from the gaseous hydrocarbon products. The gaseous hydrocarbon products can be recycled to the separation column (1). Alternatively, the gaseous hydrocarbon products can be further processed as discussed below. The liquid hydrocarbon products can be easily transported or further processed.

Figure 2:
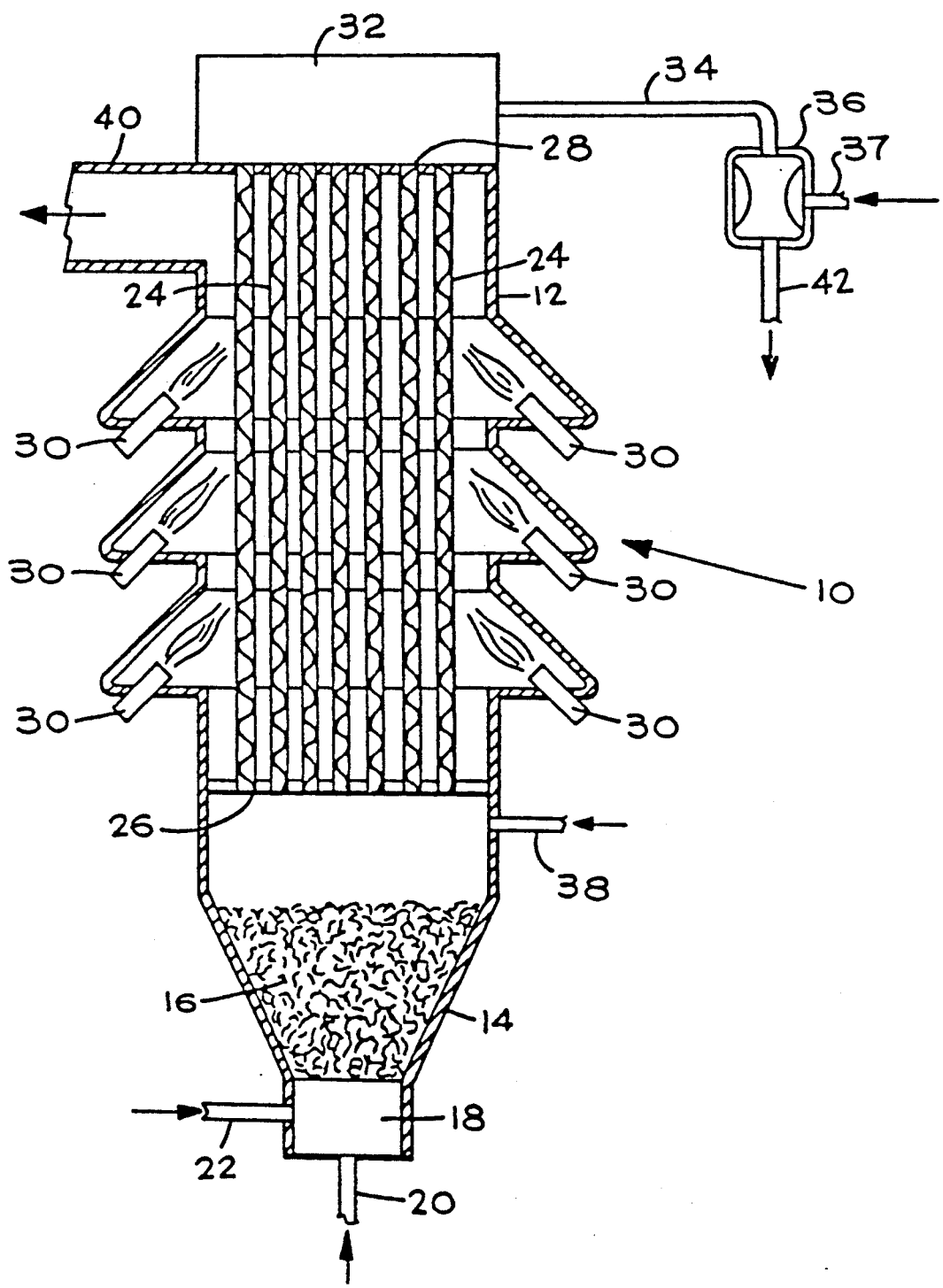
FIG. 2 is a schematic illustration of a reactor that is suitable for use in operating the process of the invention in a preferred manner.

Achievement of energy efficiency with the process of the invention can be realized by designing the reactor system in such a manner so that exothermic heat generated in the oxidative-coupling reaction is efficiently transferred to the pyrolysis reactor. Reactor systems that are suitable for use with the process of the invention can have various designs, an example of which is illustrated in FIG. 2. Referring to FIG. 2, an integrated unit 10 in which the process of the invention can be operated includes a vertical column 12 and a conical section 14. Catalyst 16 is contained within conical section 14. Catalyst 16 can be in any of the forms discussed above (e.g., fixed bed, fluid bed, spouted bed, monolith, etc.). Premix chamber 18 is mounted underneath the conical section 14, and includes inlet 20 for admitting the gaseous reactants (e.g., methane, natural gas, etc.) and inlet 22 for admitting the oxygen source (e.g., oxygen, air, etc.) into premix chamber 18. The gaseous reactant and oxygen are premixed in premix chamber 18 and preferably preheated to a temperature of up to about 700° C., more preferably about 200° C. to about 700° C. Vertical column 12 contains a plurality of vertically elongated pyrolysis reactor tubes 24 which are of conventional design and can be constructed of, for example, silicon carbide, quartz, alumina, high-temperature metal alloys, etc. Pyrolysis tubes 24 are positioned between and secured by tube sheets 26 and 28. Gas burners 30 are mounted in the side wall of column 12 and are adapted for heating the pyrolysis tubes 24. Collection header 32 is positioned above the pyrolysis tubes. Conduit 34 interconnects collection header 32 with venturi 36. The liquid or gas used to operate venturi 36 enters at inlet 37. Inlet 38 is positioned in the side wall of column 12 above catalyst 16. Column 12 also includes flue 40 for permitting an outlet of the flue gases from burners 30. Heat from the hot flue gases can be transferred using, for example, a heat exchanger to, for example, premix chamber 18 to increase the overall efficiency of the process. In operation, the gaseous reactants enter the premix chamber 18 through inlet 20. Oxygen enters the premix chamber through inlet 22. The gaseous reactants and oxygen are premixed in chamber 18 and preferably preheated. The gaseous reactants and oxygen are advanced upwardly into the conical section 14 of the reactor 10 wherein the gaseous reactants and oxygen contact catalyst 16 and undergo an oxidative-coupling reaction resulting in the formation of an intermediate product. The intermediate product and unreacted gases are advanced upwardly into pyrolysis reactor tubes 24. Additional $C_2+$ hydrocarbon reactants can be introduced into reactor 10 through inlet 38 and are also advanced upwardly through pyrolysis tubes 24. Exothermic heat from the oxidative-coupling reaction increases the temperature of the gases advancing upwardly into pyrolysis tubes 24. The gases in pyrolysis tubes 24 are heated for an effective period of time to undergo a pyrolysis reaction. If additional heat is required for the pyrolysis reaction, burners 30 are used to provide such additional heat. The pyrolyzed product is collected in collection header 32 and advanced through conduit 34 to venturi 36. The higher molecular weight hydrocarbon products are quenched in venturi 36 and exit as effluent stream 42. The products in effluent stream 42 can then be transported or further processed as discussed below.

The composition of the higher molecular weight hydrocarbon products produced in accordance with the process of the invention is somewhat dependent upon the nature of the gaseous reactants that are initially used in the feedstream, and the conditions under which they are processed. Typically, the higher molecular weight hydrocarbon product will consist of hydrocarbons containing two or more carbon atoms. These hydrocarbon products generally consist of mixtures of both aliphatic and aromatic materials. Since the process of the present invention is wellsuited to a continuous, cyclic process, the lighter weight gaseous hydrocarbon products such as ethane or propane, etc., can be separated from the more desirable higher molecular weight hydrocarbon products (generally liquid) and recycled in the process for further conversion to even higher molecular weight hydrocarbon products. Methane is preferably recycled to the oxidation-coupling zone of the reactor while the $C_2+$ hydrocarbons are preferably recycled to the pyrolysis zone of the reactor. Unsaturated hydrocarbons present in the hydrocarbon products include ethylene and acetylene which may be recovered as products of the process or recycled to the pyrolysis zone for conversion to higher molecular weight products.

Preferred higher molecular weight hydrocarbon products made by the process of the present invention include aliphatic and/or aromatic products that are sufficiently liquid to be readily handleable and transportable in conventional liquid pipeline systems. Included in this preferred group are hydrocarbons containing at least about 5 carbon atoms, more particularly, aromatic compounds containing at least 6 carbon atoms. The references in this application to "liquid hydrocarbons" is intended to include hydrocarbons that are substantially in the liquid form at a temperature of about 25° C. and a pressure of one atmosphere.

The $C_2+$ higher molecular weight hydrocarbon products that are made by the process of the invention have numerous applications in chemical processing as well as uses as fuels. For example, U.S. Pat. No. 4,100,218 discloses subjecting ethane to thermal cracking at temperatures of from about 815° C. to about 875° C. to produce an olefin-rich effluent which is then cooled to a temperature between about 315° C. and about 650° C. and contacted with a zeolite so as to produce a liquid hydrocarbon product suitable for use as LPG, gasoline and/or aromatics concentrate. U.S. Pat. No. 4,120,910 discloses converting ethane to liquid aromatic compounds with a process which comprises contacting, in the absence of added air or oxygen under conversion conditions, a gaseous paraffinic hydrocarbon feed containing ethane, with a catalyst comprising a crystalline aluminosilicate zeolite characterized by a constraint index within the approximate range of 1 to 12 and a silica to alumina ratio of at least 12, said catalyst having incorporated therein from about 0.01 to 30 weight percent based on the total weight of the catalyst of a metal or metal oxide wherein said metal is selected from the group consisting of Group VIII, IIB and IB metals and mixtures thereof whereby ethane present in said gaseous feed is converted to aromatic compounds and recovering said aromatic compounds as liquids. The foregoing patents are incorporated herein by reference. Other known processes are also available for the conversion of these higher molecular weight hydrocarbon products of the process of the invention to, for example, ethanol, ethylene glycol, polyethylene, and other additional chemicals useful as fuels, fuel additives and lubricants. Thus, the process of the invention may be integrated with another process for converting the higher molecular hydrocarbon products to useful chemicals.

In order to further illustrate the process of the invention, the following examples are provided. Unless otherwise indicated in the following examples, all parts and percentages of the products are by weight, and those of the feeds are by volume; all temperatures are in degrees centigrade.

EXAMPLES 2-4

In Examples 2A-2C a quartz tube reactor was used that consisted of two quartz tubes connected to each other and surrounded by two electric furnaces. 1.5 c.c. of the catalyst from Example 1 filled the first quartz tube, this first tube being referred to hereinafter as the oxidative-coupling zone of the reactor. The second quartz tube was surrounded by the second furnace, this second tube being referred to hereinafter as the pyrolysis zone of the reactor. In operation, the gaseous feedstream was advanced through the reactor and the effluent was collected in containers cooled with dry ice and acetone.

In Examples 3 and 4, a first quartz tube was surrounded by a first electric furnace to provide the desired temperature for the oxidative-coupling step of the reaction. 1.5 c.c. of the catalyst from Example 1 filled the first quartz tube. This first quartz tube is referred to hereinafter as the oxidative-coupling zone of the reactor. A second quartz tube reactor was positioned downstream of the first reactor and surrounded by a second electric furnace to provide the desired temperature for the pyrolysis step of the reaction. This second quartz tube is referred to hereinafter as the pyrolysis zone of the reactor.

In Examples 3A and 4A, the gaseous feedstream was advanced through the first reactor to undergo oxidative coupling. The effluent from the first reactor was cooled in an ice bath to remove water. The cooled effluent was advanced through the second reactor to undergo pyrolysis. The effluent from the second reactor was collected in containers cooled with dry ice and acetone.

In Examples 3B and 4B, the gaseous feedstream was advanced through the first reactor to undergo oxidative coupling. The effluent from the first reactor was collected in containers cooled with ice.

In Examples 3C and 4C, the gaseous feedstream was advanced through the second reactor to undergo pyrolysis. The effluent from the second reactor was collected in containers cooled with dry ice and acetone.

Examples 2A, and 4A are illustrative of the invention; these examples illustrate the use of oxidative coupling in combination with pyrolysis. Examples 2B, 3B and 4B are provided for purposes of comparison; each of these examples illustrates the use of only oxidative coupling. Note that although the gaseous reactants passed through the pyrolysis zone in Example 2B, the temperature of 200° C. was insufficient to effect a pyrolysis reaction. Examples 2C, 3C and 4C are also provided for purposes of comparison; each of these examples illustrates the use of only pyrolysis.

The results are indicated in Tables I–III. The "liquids" identified in the following tables were those materials which condensed in the cooled containers after subtracting out the water that had formed. The weight percentage of the liquid hydrocarbon products was calculated by weighing the liquids formed and dividing that weight by the amount of hydrocarbon in the feed composition and multiplying by 100. The selectivity was defined by dividing the weight of product formed by the weight of consumed hydrocarbon feed and multiplying by 100. The conversion was defined by dividing the hydrocarbon that was converted by the hydrocarbon in the feed and multiplying by 100. The gases that were obtained from the process were analyzed using a Carl 400GC gas chromatograph. The operating pressure was atmosphere pressure. The term "NA" in the tables means not applicable.

TABLE I

| Example | 2A | 2B | 2C |
|---|---|---|---|
| Feedstream (Vol %) | | | |
| Methane | 70.85 | 70.85 | 100.00 |
| Oxygen | 7.93 | 7.93 | — |
| Nitrogen | 21.23 | 21.23 | — |
| Process Conditions | | | |
| Contact Oxidative-Coupling Zone (milliseconds) | 94 | 94 | * |
| Residence time Pyrolysis Zone (milliseconds) | 292 | 820 | 292 |
| Temperature, °C. | | | |
| Oxidative-Coupling Zone | 825 | 825 | 825 |
| Pyrolysis Zone | 1050 | 200 | 1050 |
| Tube Diameter (cm) | | | |
| Oxidative-Coupling Zone | 0.8 | 0.8 | 0.8 |
| Pyrolysis Zone | 0.6 | 0.6 | 0.6 |
| Product Analysis (Wt. %) | | | |
| Methane Conversion | 21.6 | 13.2 | 0.3 |
| Selectivity to Liquids | 50.5 | 0.0 | None |
| Selectivity to $C_2^+$ Hydocarbons | 78.1 | 69.2 | — |
| Selectivity to $CO + CO_2$ | 14.5 | 26.6 | NA |
| Liquids formed (%) | 10.9 | 0.0 | Trace |

*No catalyst was used in the oxidative-coupling zone.

TABLE II

| Example | 3A | 3B | 3C |
|---|---|---|---|
| Feedstream (Vol %) | | | |
| Methane | 70.85 | 70.85 | 100.00 |
| Oxygen | 7.93 | 7.93 | — |
| Nitrogen | 21.23 | 21.23 | — |
| Process conditions | | | |
| Contact time Oxidative-Coupling Zone, (milliseconds) | 94 | 94 | NA |
| Residence time Pyrolysis Zone, (milliseconds) | 206 | NA | 204 |
| Temperature, °C. | | | |
| Oxidative-Coupling Zone | 825 | 825 | NA |
| Pyrolysis Zone | 1125 | NA | 1125 |
| Tube Diameter (cm) | | | |
| Oxidative-Coupling Zone | 0.5 | 0.5 | NA |
| Pyrolysis Zone | 0.5 | NA | 0.5 |
| Product Analysis (Wt. %) | | | |
| Methane Conversion | 28.6 | 15.7 | 3.8 |
| Selectivity to Liquids | 29.7 | 0.0 | 40.4 |
| Selectivity to $C_2^+$ Hydrocarbons | 58.6 | 75.1 | 51.2 |
| Selectivity to $CO + CO_2$ | 13.4 | 24.8 | NA |
| Liquids forced (%) | 8.5 | 0.0 | 1.5 |

TABLE III

| Example | 4A | 4B | 4C |
|---|---|---|---|
| Feedstream (Vol %) | | | |
| Methane | 70.85 | 70.85 | 100.00 |
| Oxygen | 7.93 | 7.93 | — |
| Nitrogen | 21.23 | 21.23 | — |
| Process Conditions | | | |
| Contact time Oxidative-Coupling Zone, (milliseconds) | 95 | 95 | NA |
| Residence time Pyrolysis Zone (milliseconds) | 72 | NA | 72 |
| Temperature, °C. | | | |
| Oxidative-Coupling Zone | 825 | 825 | NA |
| Pyrolysis Zone | 1125 | NA | 1125 |
| Tube Diameter (cm) | | | |
| Oxidative-Coupling Zone | 0.5 | 0.5 | NA |
| Pyrolysis Zone | 0.3 | NA | 0.3 |
| Product Analysis (Wt. %) | | | |
| Methane Conversion | 22.2 | 16.2 | Trace |
| Selectivity to Liquids | 42.6 | 0.0 | — |
| Selectivity to $C_2^+$ Hydrocarbons | 80.0 | 74.7 | — |
| Selectivity to $CO + CO_2$ | 15.0 | 22.4 | NA |
| Liquids formed (%) | 9.5 | 0.0 | Trace |

A comparison of Example 2A with Example 2B indicates significant improvements in conversion of methane, yield of liquids formed and selectivity to $C_2^+$ hydrocarbons and liquids when oxidative-coupling is used in combination with pyrolysis (Example 2A) in accordance with the invention as opposed to just oxidative-coupling (Example 2B). A comparison of Example 2A with Example 2C also indicates significant improvement in all these results with the use of oxidative-coupling in combination with pyrolysis on a feedstream containing methane, oxygen and nitrogen (Example 2A) as opposed to just the pyrolysis of pure methane (Example 2C). Example 2A also demonstrates that effective yields and conversions can be obtained at the relatively low pyrolysis temperature of 1050° C. when oxidative-coupling is used in combination with pyrolysis in accordance with the invention.

A comparison of Example 3A with Example 3B indicates significant improvements in conversion of methane and yield of liquids formed when oxidative-coupling is used in combination with pyrolysis (Example 3A) in accordance with the invention as opposed to just oxidative-coupling (Example 3B). A comparison of Example 3A with Example 3C also indicates significant improvement in each of these results with the use of oxidative-coupling in combination with pyrolysis on a feedstream containing methane, oxygen and nitrogen (Example 3A) as opposed to just the pyrolysis of pure methane (Example 3C).

A comparison of Example 4A with Example 4B indicates significant improvements in conversion of methane and yield of liquids formed when oxidative-coupling is used in combination with pyrolysis (Example 4A) in accordance with the invention as opposed to just oxidative-coupling (Example 4B). A comparison of Example 4A with Example 4C also indicates significant improvement in each of these results with the use of oxidative-coupling in combination with pyrolysis on a feedstream containing methane, oxygen and nitrogen (Example 4A) as opposed to just the trace amounts that were obtained with the pyrolysis of pure methane (Example 4C).

While the invention has been explained in relation to its preferred embodiments, it is to be understood that various modifications thereof will become apparent to those skilled in the art upon reading this specification. Therefore, it is to be understood that the invention disclosed herein is intended to cover such modifications as fall within the scope of the appended claims.

We claim:

1. A process for converting a gaseous reactant comprising methane or natural gas to higher molecular weight hydrocarbon products comprising:
   (1) contacting said gaseous reactant with an oxidative coupling catalyst at a reaction temperature in the range of about 500° C. to about 1100° C. for an effective period of time to form an intermediate product comprising ethane, ethylene or a mixture thereof; and
   (2) pyrolyzing said intermediate product at a temperature in the range of about 900° C. to about 1500° C. for an effective period of time to form said higher molecular weight hydrocarbon products using sensible heat generated during the formation of said intermediate product.

2. The process of claim 1 separating said intermediate product and said catalyst subsequent to step (1) but prior to step (2).

3. The process of claim 1 wherein said reaction temperature during step (1) is in the range of about 700° C. to about 950° C.

4. The process of claim 1 wherein said temperature during step (2) is in the range of about 950° C. to about 1300° C.

5. The process of claim 1 wherein said temperature during step (2) is in the range of about 1000° C. to about 1200° C.

6. The process of claim 1 wherein the average contact time between said gaseous reactant and said catalyst is in the range of about 1 to about 1500 milliseconds.

7. The process of claim 1 wherein the average contact time between said gaseous reactant and said catalyst is in the range of about 20 to about 1000 milliseconds.

8. The process of claim 1 wherein said pyrolysis step (2) is conducted in a reactor, the average residence time of the gases in said reactor being in the range of about 1 to about 1500 milliseconds.

9. The process of claim 1 wherein said pyrolysis step (2) is conducted in a reactor, the average residence time of the gases in said reactor being in the range of about 20 to about 1000 milliseconds.

10. The process of claim 1 conducted at a pressure in the range of about 1 to about 40 atmospheres.

11. The process of claim 1 conducted at a pressure in the range of about 1 to about 4 atmospheres.

12. The process of claim 1 wherein said gaseous reactant further comprises oxygen or an oxygen source.

13. The process of claim 1 wherein said gaseous reactant further comprises oxygen or an oxygen source, the mole ratio of oxygen to methane in said gaseous reactant being in the range of about 0.1 to about 1 mole of oxygen per mole of methane.

14. The process of claim 1 wherein said gaseous reactant comprises natural gas.

15. The process of claim 1 wherein said catalyst is a complex represented by the formula $$A_a D_b E_c O_x$$

wherein
A is selected from the group consisting of alkali metal, Ag, Tl and a mixture of two or more thereof,
D is selected from the group consisting of Mn, Sn, Pb, Sb, Bi, Zn, a rare earth metal, an alkaline earth metal, and a mixture of two or more thereof,
E is selected from the group consisting of Ti, Zr, Hf, Nb, Ta, W, Al, Si, P, Ga, B, and a mixture of two or more thereof,
a is a number in the range of zero to about 100,
b is a number in the range of about 0.1 to about 100,
c is a number in the range of zero to about 100, and
x is the number of oxygens needed to fulfill the valence requirements of the other elements.

16. The process of claim 15 wherein said metal oxide complex is supported on a carrier.

17. The process of claim 16 wherein said carrier is silica, alumina, fused alumina, zirconia, hafnia, titania, magnesia, germanium oxide, silicon carbide or clay.

18. The process of claim 15 wherein said metal oxide complex is supported on a carrier, said catalyst being prepared by the steps of (a) preparing a powdered precipitate of said metal oxide complex, (b) preparing a wetted carrier, and (c) contacting said wetted carrier with said precipitate until said catalyst is formed.

19. The process of claim 1 wherein said catalyst is a metal oxide complex represented by the formula $$PbMg_nO_x$$

wherein
n is a number in the range of about 0.1 to about 100, and
x is the number of oxygens needed to fulfill the valence requirements of the other elements.

20. The process of claim 19 wherein n is in the range of about 1 to about 30.

21. The process of claim 19 wherein n is in the range of about 10 to about 24.

22. The process of claim 1 wherein said catalyst is a metal oxide other than a reducible metal oxide.

* * * * *